(12) United States Patent
Smith

(10) Patent No.: US 10,588,852 B2
(45) Date of Patent: Mar. 17, 2020

(54) FACE AND BODY CREAM COMPOSITION

(71) Applicant: Louise M. Smith, Henderson, NV (US)

(72) Inventor: Louise M. Smith, Henderson, NV (US)

(*) Notice: Subject to any disclaimer, the term of this patent is extended or adjusted under 35 U.S.C. 154(b) by 72 days.

(21) Appl. No.: 15/889,798

(22) Filed: Feb. 6, 2018

(65) Prior Publication Data
US 2019/0240140 A1 Aug. 8, 2019

(51) Int. Cl.
| A61K 8/92 | (2006.01) |
| A61K 8/9789 | (2017.01) |
| A61Q 19/00 | (2006.01) |
| A61K 8/9794 | (2017.01) |
| A61K 36/185 | (2006.01) |
| A61K 36/63 | (2006.01) |
| A61K 36/47 | (2006.01) |

(52) U.S. Cl.
CPC ............ *A61K 8/9789* (2017.08); *A61K 8/922* (2013.01); *A61K 8/9794* (2017.08); *A61K 36/185* (2013.01); *A61K 36/47* (2013.01); *A61K 36/63* (2013.01); *A61Q 19/00* (2013.01); *A61K 2800/5922* (2013.01)

(58) Field of Classification Search
CPC .......... A61K 8/02; A61K 8/0216; A61K 8/04; A61K 8/042; A61K 8/044; A61K 8/046; A61K 8/06; A61K 8/73; A61K 8/732; A61K 8/92; A61K 8/922; A61K 8/925; A61K 8/96; A61K 8/98; A61K 8/986; A61K 8/987
See application file for complete search history.

(56) References Cited

U.S. PATENT DOCUMENTS

| 8,075,901 B1 | 12/2011 | Waters |
| 8,449,895 B1 | 5/2013 | Koiteh |
| 9,474,709 B2 | 10/2016 | Sams |
| 2006/0147390 A1 | 7/2006 | Schreiber et al. |
| 2007/0280898 A1 | 12/2007 | Riddle |
| 2009/0130220 A1 | 5/2009 | Johnson |
| 2012/0276030 A1* | 11/2012 | Marthaler ................ A61Q 1/02 424/63 |
| 2013/0303631 A1* | 11/2013 | Quan ..................... A61K 8/645 514/773 |
| 2014/0248370 A1 | 9/2014 | Ali |
| 2015/0328222 A1 | 11/2015 | Tortoriello et al. |
| 2016/0317576 A1 | 11/2016 | Rosanoff |

OTHER PUBLICATIONS

Bonbons Cheveux, Mint Chocolate Hair Icing 100% Natural, Mar. 23, 2016 [retrieved on Mar. 5, 2019]. Retrieved from Internet: <URL: https://web.archive.org/web/20160323011127/http://store.bonbonscheveux.com/product/pepper mint-hair-icing-new-improved?>.

* cited by examiner

*Primary Examiner* — Micah Paul Young
(74) *Attorney, Agent, or Firm* — Olav M. Underdal; IDP Patent Services

(57) ABSTRACT

A face and body cream composition includes: rhea butter, coconut oil, cocoa butter, castor oil, avocado oil, aloe vera, olive oil, frankincense oil, bergamot oil, and camphor oil; that is whipped to include a homogenous distribution of a plurality of air micro bubbles. Also disclosed is a method for manufacturing, including mixing base ingredients, adding secondary ingredients, whipping all ingredients, and cooling face and body cream composition.

22 Claims, 1 Drawing Sheet

Method for Manufacturing Face and Body Cream Composition
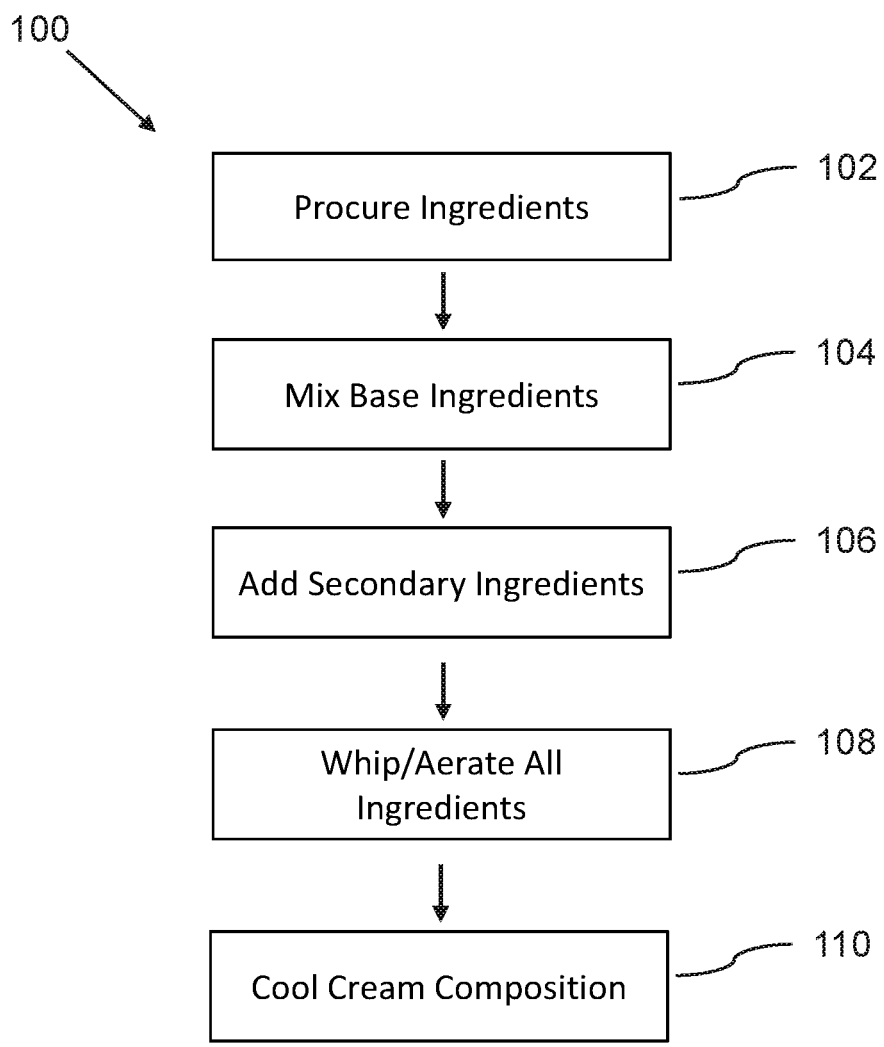

FACE AND BODY CREAM COMPOSITION

CROSS-REFERENCE TO RELATED APPLICATIONS

N/A.

FIELD OF THE INVENTION

The present invention relates generally to the field of face and body creams, and more particularly to face and body creams that include shea butter and a combination of oils.

BACKGROUND OF THE INVENTION

Face and body cream combinations with shea butter are popular due to the healing and soothing properties of shea butter.

However, such creams tend to have an oily character, and may not be easily absorbable by the skin.

As such, considering the foregoing, it may be appreciated that there continues to be a need for novel and improved devices and methods for face and body creams.

SUMMARY OF THE INVENTION

The foregoing needs are met, to a great extent, by the present invention, wherein in aspects of this invention, enhancements are provided to the existing model of face and body creams.

In an aspect, a face and body cream composition can include:
a) shea butter;
b) coconut oil;
c) cocoa butter;
d) castor oil;
e) avocado oil;
f) aloe vera; and
g) olive oil.

In a related aspect, the face and body cream composition of can further include frankincense oil, bergamot oil, and camphor oil.

In a further related aspect, the face and body cream composition can include:
a) the raw rhea butter in a range of 24-72 percent by weight of the face and body cream composition;
b) the coconut oil in a range of 8-24 percent by weight of the face and body cream composition;
c) the cocoa butter in a range of 6-16 percent by weight of the face and body cream composition;
d) the castor oil in a range of 2-6 percent by weight of the face and body cream composition;
e) the avocado oil in a range of 1-3 percent by weight of the face and body cream composition;
f) the aloe vera in a range of 5-15 percent by weight of the face and body cream composition;
g) the olive oil in a range of 2-6 percent by weight of the face and body cream composition;
h) the frankincense oil in a range of 0.1-0.6 percent by weight of the face and body cream composition;
i) the bergamot oil in a range of 0.1-0.6 percent by weight of the face and body cream composition; and
j) the camphor oil in a range of 1.5-6 percent by weight of the face and body cream composition.

In another related aspect, the face and body cream composition can further include a homogenous distribution of a plurality of ambient air micro bubbles.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 1 is a flowchart illustrating steps that may be followed, in accordance with one embodiment of a method or process of manufacturing a face and body cream composition.

DETAILED DESCRIPTION

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

In an embodiment, a face and body cream composition can include:
a) Shea butter, a fat extracted from the nut of the African shea tree (*Vitellaria paradoxa*), which can be a raw shea butter;
b) Coconut oil, an oil extracted from the kernel or meat of coconuts harvested from the coconut palm (*Cocos nucifera*), which be an unrefined cold pressed coconut oil;
c) Cocoa butter, also called *theobroma* oil, a pale-yellow, edible vegetable fat extracted from the cocoa bean;
d) Castor oil, which can be cold pressed;
e) Avocado oil, which can be cold pressed;
f) Aloe vera, which can be a gel made from whole leaf aloe vera;
g) Olive oil;

h) Frankincense oil, an aromatic resin from trees of the genus *Boswellia* in the family Burseraceae, including *Boswellia sacra, B. carterii, B. frereana, B. serrata,* and *B. papyrifera;*
i) Bergamot oil; and
j) Camphor oil.

The face and body cream composition can also be referred to as a cream composition, skin cream composition, or body cream composition.

In related embodiments, each oil of the face and body cream composition provide a distinct set of benefits and healing properties and in combination the synergy of blending them is most powerful. The health benefits of the blended oils include properties such as antiseptic, antineuralgic, anti-inflammatory, disinfectant, anti-aging, anti-wrinkle, free radical skin protectant, antioxidant, and many other health benefits.

In related embodiments, the face and body cream composition can be used for relief of proctitis, acute fissures, swollen hemorrhoids, and rectal pain or discomfort; and to promote healthy youthful looking skin, to assist with skin diseases as well as bacterial and fungal infections and inflammatory condition of the skin such as eczema and psoriasis.

In other related embodiments, the face and body cream composition, can provide quick relief from painful burning, itching and discomfort of swollen hemorrhoidal tissue.

In related embodiments, benefits of raw rhea butter, include:
a) Providing a skin nutrient that is naturally rich in vitamins a, e and f, and provides the skin with essential fatty acids and the nutrients necessary for collagen;
b) Treatment for acne and blemishes;
c) Function as a skin moisturizer
d) Anti-inflammatory properties
e) Antioxidants which reduce free radicals
f) Contains vitamins a, and e which protects the skin from sun damage
g) Function as a sun blocker (including UV protection);
h) Provides relief for insect bites;
i) Provides relief of itchy and peeling skin;
j) Restores the elasticity of skin;
k) Reduces razor irritation and bumps;
l) Reduces stretch marks;
m) Soothes skin and baby diaper rash; and
n) Provides relief for conditions such as dermatitis, psoriasis, and eczema.

In related embodiments, benefits of coconut oil include:
a) Retains moisture content of skin;
b) Protects skin from microbial infections;
c) Provides comfort to chapped dry skin;
d) Repairs skin and gives it a healthy glow;
e) Provides relief for skin disorders such as acne, psoriasis and eczema;
f) Promotes skin renewal;
g) Treats skin discoloration (dark spots removal);
h) Functions as skin softener
i) Anti-aging properties;
j) Anti-wrinkle functions;
k) Relief for skin disorders;
l) Skin clear completion;
m) Anti-inflammation
n) Exfoliant
o) Treats stretch marks;
p) Treats hardened and cracked feet;
q) Antibacterial;
r) Antifungal;
s) Restores gums and functions as teeth whitener; and
t) Unclogs skin pores.

In related embodiments, benefits of cocoa butter include:
a) Provides thickness and smoothness to the face and body cream composition;
b) Helps alleviate sunburn;
c) Prevents skin dryness;
d) Alleviates skin rashes;
e) Alleviates skin peeling;
f) May improve heart health; and
g) May raise immune system response.

In related embodiments, benefits of castor oil include:
a) Heals inflamed skin;
b) Fights signs of aging;
c) Reduces acne;
d) Moisturizes skin;
e) Fades blemishes;
f) Prevents stretch marks;
g) Reduces pigmentation;
h) Disinfects wounds;
i) Reduces signs of aging; and
j) Helps with ringworms.

In related embodiments, benefits of avocado oil include:
a) Smoothes skin
b) Moisturizes skin;
c) Acne treatment
d) Anti-aging
e) Functions as sunscreen
f) Reduces itching and inflammation
g) Boosts collagen production;
h) Soothes sunburned skin;
i) Aides in wound treatment;
j) Prevents sun damage;
k) Antioxidant;
l) Reduces dark circles under eyes; and
m) Alleviates eczema and psoriasis.

In related embodiments, benefits of aloe vera gel include:
a) aloe vera gel contains two hormones, auxin and gibberellin, which provide wound healing and anti-inflammatory properties that reduce skin inflammation;
b) Treats skin psoriasis;
c) Treats acne;
d) Treats eczema;
e) Soothes sunburns;
f) Repairs dry skin;
g) Anti-wrinkle properties;
h) Heals external wounds;
i) Reduces stretch marks;
j) Reduces inflammation;
k) Improves oral health;
l) Treating hemorrhoids;
m) Reduces swollen tissue vessels;
n) Moisturizes skin;
o) Helps lighten blemishes; and
p) Tighten skin.

In related embodiments, benefits of olive oil include:
a) Anti-aging;
b) Antioxidants;
c) Contains hydrating squalene;
d) Softens and smooths repair skin damage;
e) Contains antioxidants vitamins a and e, which repair sun damage, and effects on skin from cigarette smoke and air pollutants;
f) Reduce wrinkles;
g) Alleviates cracked heels;
h) Moisturizes skin;
i) Reduces inflammation;

j) Functions as exfoliant;
k) Treats psoriasis; and
l) Lightens the skin.

In related embodiments, benefits of frankincense oil include:
a) Promotes gum health;
b) Anti-aging;
c) Anti-wrinkle;
d) Alleviates razor bumps;
e) Skin rejuvenator; promotes healthy cellular function;
f) Powerful astringent;
g) Reduces acne;
h) Lifts and tighten skin;
i) Reduce the appearance of large pores;
j) Treats skin burns and skin rashes;
k) Treats skin cuts;
l) Treats oozing sores;
m) Great for most skin care;
n) Treats insect bites;
o) Protect skin cells; and
p) Strengthens gums In related embodiments, benefits of bergamot oil include:
a) Natural skin cleanser properties;
b) Removes dirt and impurities
c) Helps unclog pores;
d) Balance oily skin;
e) Sunscreen;
f) Skin tightening;
g) Removes dark circles under eyes
h) Reduces scars;
i) Removes acne marks;
j) lightens dark spots
k) Promotes even distribution of melanin
l) Anti-microbial;
m) Alleviates muscle pain;
n) Promotes dental health;
o) Tightens loose skin;
p) Antiseptic properties;
q) Anti-inflammatory properties; and
r) Anti-scarring properties.

In related embodiments, benefits of camphor oil include:
a) Stimulant properties;
b) Antispasmodic properties;
c) Antiseptic properties;
d) Anesthetic properties;
e) Antineuralgic properties;
f) Anti-inflammatory properties;
g) Disinfectant properties;
h) Improves circulation;
i) Prevents skin infections;
j) Relieves spasms;
k) Relieves neuralgia;
l) Boosts the libido;
m) Treats bacterial and fungal infections of the skin;
n) Promotes blood vessel contraction; and
o) Provides cooling sensation.

In a related embodiment, the face and body cream composition can include all raw natural untreated ingredients, including:
a) raw shea butter in an amount of 24 ounces;
b) unrefined pressed coconut oil in an amount of 8 ounces;
c) cocoa butter in an amount of 6 ounces;
d) cold press castor oil in an amount of 2 ounces;
e) cold press avocado oil in an amount of 1 ounces;
f) aloe vera gel in an amount of 5 ounces;
g) cold pressed olive oil in an amount of 2 ounces;
h) pure frankincense oil in an amount of 5 milliliters;
i) pure bergamot oil in an amount of 5 milliliters; and
j) pure camphor oil in an amount of 3-5% by volume.

In a related embodiment, the face and body cream composition can include:
a) raw shea butter in a range of 12-36 ounces;
b) unrefined pressed coconut oil in a range of 4-12 ounces;
c) cocoa butter in a range of 3-9 ounces;
d) cold press castor oil in a range of 1-3 ounces;
e) cold press avocado oil in a range of 0.5-1.5 ounces;
f) aloe vera gel in a range of 2.5-7.5 ounces;
g) cold pressed olive oil in a range of 1-3 ounces;
h) pure frankincense oil in a range of 0.08-0.23 ounces;
i) pure bergamot oil in a range of 0.08-0.23 ounces; and
j) pure camphor oil in a range of 0.8-2.5 ounces.

In another related embodiment, the face and body cream composition can include:
a) rhea butter in a range of 24-72 percent by weight of the face and body cream composition;
b) coconut oil in a range of 8-24 percent by weight of the face and body cream composition;
c) cocoa butter in a range of 6-18 percent by weight of the face and body cream composition;
d) castor oil in a range of 2-6 percent by weight of the face and body cream composition;
e) avocado oil in a range of 1-3 percent by weight of the face and body cream composition;
f) aloe vera gel in a range of 5-15 percent by weight of the face and body cream composition;
g) olive oil in a range of 2-6 percent by weight of the face and body cream composition;
h) frankincense oil in a range of 0.1-0.6 percent by weight of the face and body cream composition;
i) bergamot oil in a range of 0.1-0.6 percent by weight of the face and body cream composition; and
j) camphor oil in a range of 1.5-6 percent by weight of the face and body cream composition.

In related embodiment, the shea butter absorbs the oils thereby giving the face and body cream composition a creamy consistency, rather than oily.

In related embodiments, the mixture can be made by whipping the ingredients, to giving it a soft, fluffy, and creamy feel. The whipping gives it a fast vortex speed which allows oxygen/air to enter the mixture, such that the mixture is aerated, which will lighten the texture and stabilize air bubbles in the mixtures. The whipping process completes the cream, without any additives, by oxygenating/aerating the face and body cream composition, such that the face and body cream composition comprises a homogenous distribution of ambient air micro bubbles, with a diameter in a range of 1-100 micrometer, and most commonly in range of 3-12 micrometer.

In related embodiments, the shea butter changes the consistency of the face and body cream composition from liquid to a solid, and makes the face and body cream composition more of a creamy moisturizer that is not oily. All of the vitamins and minerals are contained in the included oils, such that the composition is all natural with no added vitamins or minerals. It is not oily, and absorbs quickly in to the skin. The face and body cream composition must be stored in a cool place, with no exposure to high temperatures, such as over 80 degrees Fahrenheit.

In an embodiment, as illustrated in FIG. 1, a method for manufacturing a face and body cream composition 100, can include:

a) procuring ingredients 102, wherein the ingredients comprise:
  i. Base Ingredients:
    1) Shea butter, which can be a raw rhea butter;
    2) Coconut oil, which can be an unrefined cold pressed coconut oil; and
    3) Cocoa butter;
  ii. Secondary Ingredients:
    1) Castor oil, which can be cold pressed;
    2) Avocado oil, which can be cold pressed;
    3) Aloe vera, which can be a gel made from whole leaf aloe vera;
    4) Olive oil;
    5) Frankincense oil;
    6) Bergamot oil; and
    7) Camphor oil; and
b) Mixing base ingredients 104, wherein the rhea butter, coconut oil, and cocoa butter is mixed/whipped at a first speed, which can be at a low speed setting, in a range of 50 to 150 RPM, for a first predetermined time period, which can be in a range of 30 to 180 seconds;
c) Adding secondary ingredients 106, wherein the secondary ingredients are added to the whipped base ingredients;
d) Whipping all/combined ingredients 108, wherein all/ the combined ingredients are whipped/mixed at a second speed, which can be at a high speed setting, in a range of 150-400 RPM, for a second predetermined time period, which can be in range of 120 to 480 seconds, such that the ingredients are mixed and whipped to aerate the mixed ingredients, such that the ingredients after whipping form a face and body cream composition with a homogenous distribution of ambient air micro bubbles, with a diameter in a range of 1-100 micrometer; and
  e) Cooling cream composition 110, wherein the face and body cream composition is left to rest at an ambient temperature in a range of 60-72 Fahrenheit, for a third time period, which can be in a range of 30 to 240 minutes, to cool the face and body cream composition, such that the face and body cream composition changes state from a liquid form to a cream form. The face and body cream composition should then be stored with limited light exposure and at an ambient temperature in a range of 60-72 degrees Fahrenheit.

Here has thus been described a multitude of embodiments of the face and body cream composition, and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

Many such alternative configurations are readily apparent, and should be considered fully included in this specification and the claims appended hereto. Accordingly, since numerous modifications and variations will readily occur to those skilled in the art, the invention is not limited to the exact construction and operation illustrated and described, and thus, all suitable modifications and equivalents may be resorted to, falling within the scope of the invention.

What is claimed is:

1. A face and body cream composition, comprising:
  a) shea butter;
  b) coconut oil;
  c) cocoa butter;
  d) castor oil;
  e) avocado oil;
  f) aloe vera; and
  g) olive oil;
  wherein the face and body cream composition comprises:
    the shea butter in a range of 24-72 percent by weight of the face and body cream composition;
    the coconut oil in a range of 8-24 percent by weight of the face and body cream composition;
    the cocoa butter in a range of 6-18 percent by weight of the face and body cream composition;
    the castor oil in a range of 2-6 percent by weight of the face and body cream composition;
    the avocado oil in a range of 1-3 percent by weight of the face and body cream composition;
    the aloe vera in a range of 5-15 percent by weight of the face and body cream composition; and
    the olive oil in a range of 2-7 percent by weight of the face and body cream composition.

2. The face and body cream composition of claim 1, further comprising frankincense oil.

3. The face and body cream composition of claim 1, further comprising bergamot oil.

4. The face and body cream composition of claim 1, further comprising camphor oil.

5. The face and body cream composition of claim 1, further comprising frankincense oil, bergamot oil, and camphor oil.

6. The face and body cream composition of claim 1, comprising:
  a) the shea butter in an amount of 24 ounces;
  b) the coconut oil in an amount of 8 ounces;
  c) the cocoa butter in an amount of 6 ounces;
  d) the castor oil in an amount of 2 ounces;
  e) the avocado oil in an amount of 1 ounces;
  f) the aloe vera in an amount of 5 ounces; and
  g) the olive oil in an amount of 2 ounces.

7. The face and body cream composition of claim 5, comprising:
  a) the shea butter in an amount of 24 ounces;
  b) the coconut oil in an amount of 8 ounces;
  c) the cocoa butter in an amount of 6 ounces;
  d) the castor oil in an amount of 2 ounces;
  e) the avocado oil in an amount of 1 ounces;
  f) the aloe vera in an amount of 5 ounces;
  g) the olive oil in an amount of 2 ounces;
  h) the frankincense oil in an amount of 5 milliliters;
  i) the bergamot oil in an amount of 5 milliliters; and
  j) the camphor oil in an amount of 3-5 percent by volume of the face and body cream composition.

8. The face and body cream composition of claim 5, comprising:
  a) the frankincense oil in a range of 0.1-0.6 percent by weight of the face and body cream composition;
  b) the bergamot oil in a range of 0.1-0.6 percent by weight of the face and body cream composition; and
  c) the camphor oil in a range of 1.5-6 percent by weight of the face and body cream composition.

9. The face and body cream composition of claim 1, further comprising a homogenous distribution of a plurality of air micro bubbles.

10. The face and body cream composition of claim 9, wherein each air micro bubble in the plurality of air micro bubbles has a diameter in a range of 1-100 micrometers.

11. The face and body cream composition of claim 9, wherein each air micro bubble in the plurality of air micro bubbles has a diameter in a range of 3-12 micrometers.

12. A face and body cream composition, comprising:
a) rhea butter;
b) coconut oil;
c) cocoa butter;
d) castor oil;
e) avocado oil;
f) aloe vera;
g) olive oil;
h) frankincense oil;
i) bergamot oil; and
j) camphor oil;
wherein the face and body cream composition further comprises a homogenous distribution of a plurality of air micro bubbles;
wherein the face and body cream composition comprises:
the rhea butter in a range of 24-72 percent by weight of the face and body cream composition;
the coconut oil in a range of 8-24 percent by weight of the face and body cream composition;
the cocoa butter in a range of 6-18 percent by weight of the face and body cream composition;
the castor oil in a range of 2-6 percent by weight of the face and body cream composition;
the avocado oil in a range of 1-3 percent by weight of the face and body cream composition;
the aloe vera in a range of 5-15 percent by weight of the face and body cream composition; and
the olive oil in a range of 2-7 percent by weight of the face and body cream composition.

13. The face and body cream composition of claim 12, wherein each air micro bubble in the plurality of air micro bubbles has a diameter in a range of 1-100 micrometers.

14. The face and body cream composition of claim 12, wherein each air micro bubble in the plurality of air micro bubbles has a diameter in a range of 3-12 micrometers.

15. A method for manufacturing a face and body cream composition, comprising:
a) mixing base ingredients wherein rhea butter, coconut oil, and cocoa butter is mixed at a first speed for a first predetermined time period;
b) adding secondary ingredients, wherein the secondary ingredients are added to the mixed base ingredients, wherein the secondary ingredients comprise castor oil, avocado oil, aloe vera, and olive oil;
c) whipping combined ingredients, wherein the combined ingredients are whipped at a second speed, for a second predetermined time period, such that the combined ingredients are aerated, such that the combined ingredients after whipping form the face and body cream composition with a homogenous distribution of air micro bubbles; and
d) cooling the face and body cream composition, wherein the face and body cream composition is left to rest at an ambient temperature for a third time period, to cool the face and body cream composition;
wherein the first speed is in a range of 50 to 150 rotations per minute, and the first predetermined time period is in a range of 30 to 180 seconds;
wherein the second speed is in a range of 150-400 rotations per minute, and the second predetermined time period is in range of 120 to 480 seconds; and
wherein the first speed is lower than the second speed.

16. The method of claim 15, wherein the secondary ingredients further comprise frankincense oil, bergamot oil, and camphor oil.

17. The method of claim 15, wherein the ambient temperature is in a range of 60-72 degrees Fahrenheit, and the third time period is in a range of 30 to 240 minutes.

18. The method of claim 15, wherein:
a) the shea butter is in a range of 24-72 percent by weight of the face and body cream composition;
b) the coconut oil is in a range of 8-24 percent by weight of the face and body cream composition;
c) the cocoa butter is in a range of 6-18 percent by weight of the face and body cream composition;
d) the castor oil is in a range of 2-6 percent by weight of the face and body cream composition;
e) the avocado oil is in a range of 1-3 percent by weight of the face and body cream composition;
f) the aloe vera is in a range of 5-15 percent by weight of the face and body cream composition; and
g) the olive oil is in a range of 2-7 percent by weight of the face and body cream composition.

19. The method of claim 16, wherein:
a) the shea butter is in a range of 24-72 percent by weight of the face and body cream composition;
b) the coconut oil is in a range of 8-24 percent by weight of the face and body cream composition;
c) the cocoa butter is in a range of 6-18 percent by weight of the face and body cream composition;
d) the castor oil is in a range of 2-6 percent by weight of the face and body cream composition;
e) the avocado oil is in a range of 1-3 percent by weight of the face and body cream composition;
f) the aloe vera is in a range of 5-15 percent by weight of the face and body cream composition;
g) the olive oil is in a range of 2-7 percent by weight of the face and body cream composition;
h) the frankincense oil is in a range of 0.1-0.6 percent by weight of the face and body cream composition;
i) the bergamot oil is in a range of 0.1-0.6 percent by weight of the face and body cream composition; and
j) the camphor oil is in a range of 1.5-6 percent by weight of the face and body cream composition.

20. A method for manufacturing a face and body cream composition, comprising:
a) mixing base ingredients wherein rhea butter, coconut oil, and cocoa butter is mixed at a first speed for a first predetermined time period;
b) adding secondary ingredients, wherein the secondary ingredients are added to the mixed base ingredients, wherein the secondary ingredients comprise castor oil, avocado oil, aloe vera, and olive oil;
c) whipping combined ingredients, wherein the combined ingredients are whipped at a second speed, for a second predetermined time period, such that the combined ingredients are aerated, such that the combined ingredients after whipping form the face and body cream composition with a homogenous distribution of a plurality of air micro bubbles; and
d) cooling the face and body cream composition, wherein the face and body cream composition is left to rest at an ambient temperature for a third time period, to cool the face and body cream composition;
wherein the face and body cream composition comprises:
the rhea butter in a range of 24-72 percent by weight of the face and body cream composition;
the coconut oil in a range of 8-24 percent by weight of the face and body cream composition;
the cocoa butter in a range of 6-18 percent by weight of the face and body cream composition;

the castor oil in a range of 2-6 percent by weight of the face and body cream composition;

the avocado oil in a range of 1-3 percent by weight of the face and body cream composition;

the aloe vera in a range of 5-15 percent by weight of the face and body cream composition; and the olive oil in a range of 2-7 percent by weight of the face and body cream composition.

21. The method for manufacturing a face and body cream composition of claim 20, wherein each air micro bubble in the plurality of air micro bubbles has a diameter in a range of 1-100 micrometers.

22. The method for manufacturing a face and body cream composition of claim 20, wherein each air micro bubble in the plurality of air micro bubbles has a diameter in a range of 3-12 micrometers.

* * * * *